(12) United States Patent
Carranza et al.

(10) Patent No.: US 7,014,618 B2
(45) Date of Patent: **\*Mar. 21, 2006**

(54) SURGICAL MEASUREMENT TOOL

(75) Inventors: Jose R. Carranza, South San Francisco, CA (US); Scott O. Chamness, Menlo Park, CA (US); Theodore M. Bender, San Francisco, CA (US); Bernard A. Hausen, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/678,848

(22) Filed: Oct. 3, 2003

(65) Prior Publication Data

US 2004/0097835 A1    May 20, 2004

Related U.S. Application Data

(63) Continuation of application No. 10/041,542, filed on Jan. 7, 2002, now Pat. No. 6,666,832.

(51) Int. Cl.
*A61B 5/103* (2006.01)
*A61B 5/117* (2006.01)

(52) U.S. Cl. .................... 600/587; 33/511; 33/512

(58) Field of Classification Search ............. 600/587; 33/511, 512, 514.1
See application file for complete search history.

(56) References Cited

U.S. PATENT DOCUMENTS

| | | | | |
|---|---|---|---|---|
| 363,331 | A | * | 5/1887 | Hammer ................. 7/138 |
| 1,275,802 | A | | 8/1918 | Wallace |
| 2,896,333 | A | | 7/1959 | Kivela |
| 3,722,104 | A | | 3/1973 | Enzetti |
| 3,993,045 | A | | 11/1976 | Ion |
| 4,312,363 | A | * | 1/1982 | Rothfuss et al. ........... 600/587 |
| 5,251,642 | A | | 10/1993 | Handlos |
| 5,895,353 | A | | 4/1999 | Lunsford et al. |
| 6,110,200 | A | | 8/2000 | Hinnenkamp et al. |
| 6,485,496 | B1 | | 11/2002 | Suyker et al. |
| 6,513,254 | B1 | | 2/2003 | Lunn |
| 6,666,832 | B1 | * | 12/2003 | Carranza et al. ........... 600/587 |
| 2002/0162238 | A1 | | 11/2002 | Bakke et al. |

\* cited by examiner

*Primary Examiner*—Max F. Hindenburg
*Assistant Examiner*—Jonathan Foreman
(74) *Attorney, Agent, or Firm*—Brian A. Schar

(57) ABSTRACT

A single measurement tool is configured to measure at least one characteristic of a tubular tissue structure during a surgical procedure. The measurement tool may include an indentation defined therein that is placed against a tubular structure such as the aorta to determine whether that tubular structure has a radius larger than or smaller than the radius of curvature of the indentation. The measurement tool may include a number of first recesses for measuring the diameter of a tubular structure. The measurement tool may include at least one second recess for measuring the wall thickness of a tubular structure.

10 Claims, 3 Drawing Sheets

SURGICAL MEASUREMENT TOOL

This application is a continuation of U.S. patent application Ser. No. 10/041,542, filed on Jan. 7, 2002, now U.S. Pat. No. 6,666,832.

FIELD OF THE INVENTION

The present invention relates generally to a measurement tool adapted to measure the characteristics of at least one tubular structure within or extracted from a patient.

BACKGROUND

A coronary artery bypass graft (CABG) procedure is a common surgical procedure in which a graft vessel, such as a saphenous vein or mammary artery, is connected surgically to two target vessels. Traditionally, the diameter of the aorta, the diameter of the graft vessel, and the wall thickness of the graft vessel are not measured during CABG surgery. Instead, the surgeon visually inspects the diameter of the aorta and the diameter of the graft vessel, and disregards the wall thickness of the graft vessel. While such inspection may be adequate for suture-based anastomosis on a stopped heart, it may be inadequate when anastomotic connectors and deployment systems are used.

SUMMARY

In one aspect of the invention, a single measurement tool is configured to measure at least two characteristics of a patient's vasculature during a surgical procedure such as a coronary artery bypass graft procedure. By providing a single measurement tool to perform multiple measurements, the number of tools needed in the operating room during a surgical procedure is reduced, and space on the surgical tray is conserved.

In another aspect of the invention, the measurement tool may include an indentation defined in it, where that indentation has a radius of curvature. This indentation may be located at one end of the tool, or at another location on the tool. The indentation is placed against a tubular element such as the aorta or another artery to determine whether that tubular element has a diameter larger than or smaller than the radius of curvature of the indentation. Thus, it can be determined easily whether the diameter of the tubular element is larger than or smaller than a threshold value.

In another aspect of the invention, the measurement tool may include one or more first recesses. The first recesses each have a different width. By inflating or otherwise expanding a tubular structure extracted from a patient, that tubular element expands substantially to its in-vivo diameter. By attempting to place the tubular structure into a first recess, it can be determined whether its diameter is larger than, smaller than or substantially equal to the width of that first recess. Where multiple first recesses are provided, each has a different width, and the tubular structure can be placed successively into them in order to determine its diameter easily and quickly.

In another aspect of the invention, the measurement tool may include at least one second recess. A tubular structure extracted from a patient is allowed to remain in its natural state. That is, it is not inflated. When it is placed into a second recess, its walls are pushed together, and the lumen of the tubular structure is closed or substantially restricted. The walls of the tubular structure are substantially the same thickness, so the wall thickness measured by a second recess of a particular width is substantially half of the width of that second recess. By attempting to place the tubular structure into a second recess, it can be determined whether its wall thickness is larger than, smaller than or substantially equal to a particular value. Where multiple second recesses are provided, each has a different width, and the tubular structure can be placed successively into them in order to determine its wall thickness easily and quickly.

BRIEF DESCRIPTION OF THE DRAWINGS

The use of the same reference symbols in different figures indicates similar or identical items.

DETAILED DESCRIPTION

Figure 1:
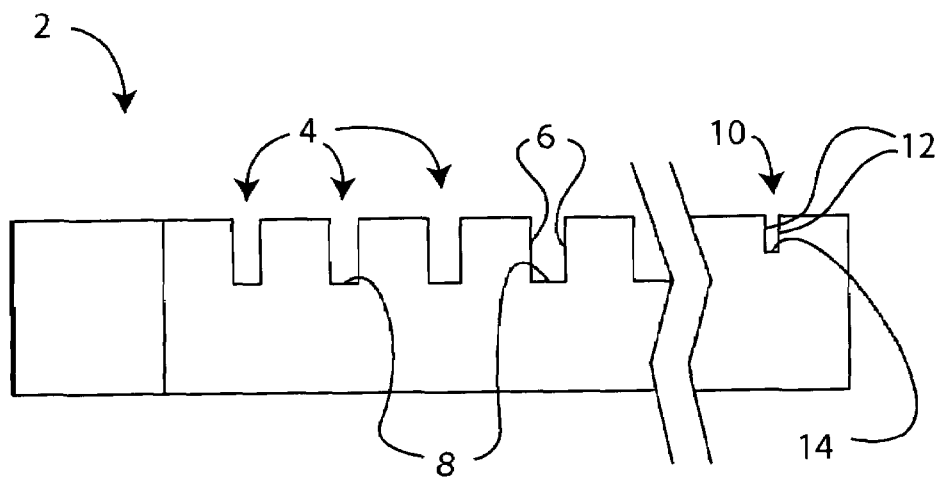
FIG. 1 is a side view of the measurement tool.
Figure 2:
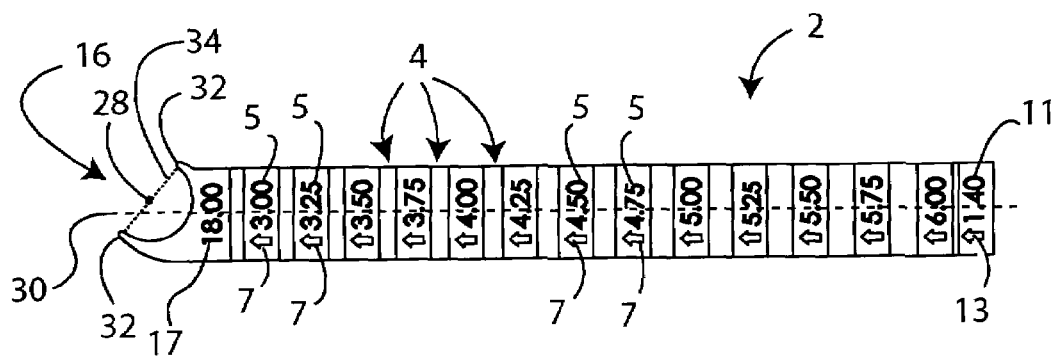
FIG. 2 is a top view of the measurement tool.
Figure 3:
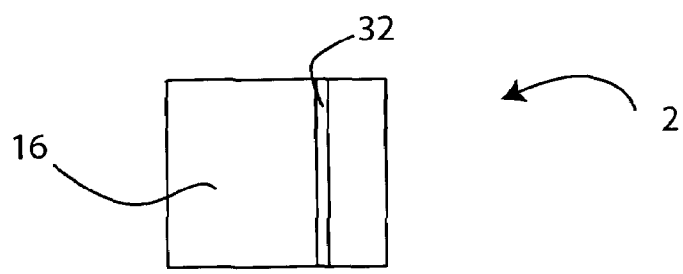
FIG. 3 is a front view of the measurement tool.
Figure 4:
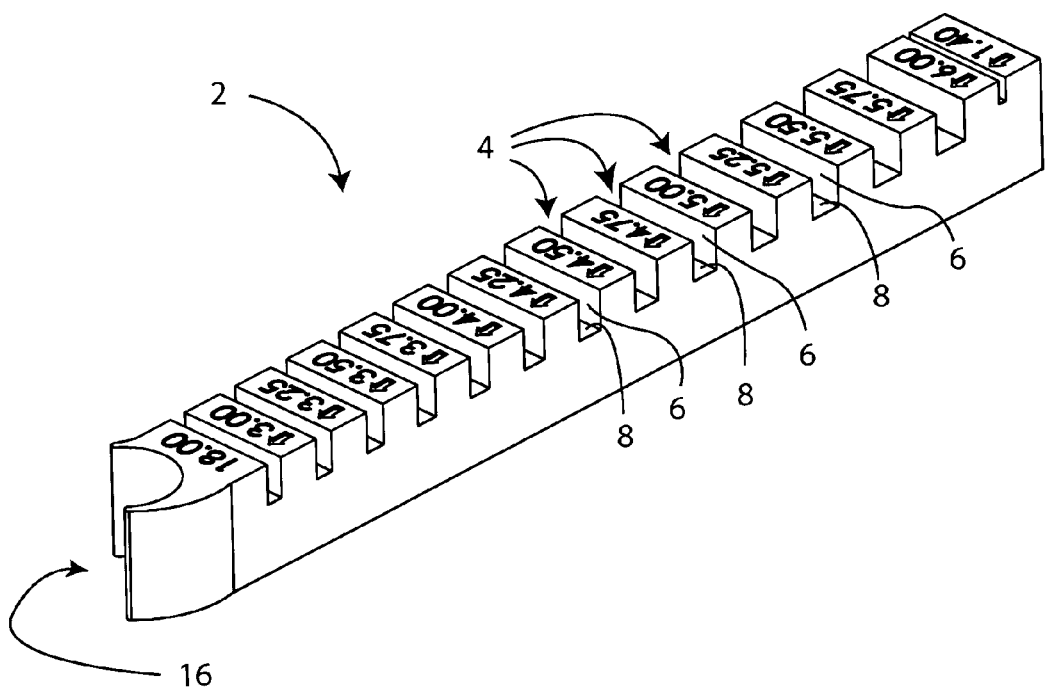
FIG. 4 is a perspective view of the measurement tool.

Referring to FIGS. 1–4, a measurement tool 2 is shown. The measurement tool 2 is a rectangular solid that is substantially as tall as it is wide, with one or more items defined therein as described below. However, the measurement tool 2 may be made thinner or thicker, or shorter or taller, if desired. Further, the measurement tool 2 need not be a rectangular solid, and may take any other shape in which one or more items described below can be defined. For example, the measurement tool 2 may be a triangular solid, a hexagonal solid, an ovoid, or other shape. Further, the measurement tool 2 may take a more complex shape, or be combined into another tool. The measurement tool 2 is constructed from polyetherimide (PEI). Alternately, the measurement tool 2 may be composed of any biocompatible material that can be sterilized for use in an operating room or other surgical setting.

At least one first recess 4 is defined in the measurement tool 2. The first recess or recesses 4 are defined in the upper surface of the measurement tool 2, but instead could be defined in a side surface or in the bottom surface of the measurement tool 2. Alternately, where multiple first recesses 4 are provided, one or more first recesses 4 may be defined in a different surface of the measurement tool 2 than one or more other first recesses 4. Each first recess 4 has two sides 6 that are substantially parallel to one another. A bottom surface 8 of each first recess 4 is substantially perpendicular to both sides 6 of the first recess 4. However, the bottom surface 8 of at least one first recess 4 may be curved such that its sides 6 smoothly transition into a bottom surface 8 substantially without corners. The curved bottom surface 8 may have a semicircular cross-section or other cross-section. If multiple first recesses 4 are provided, each has a different width from the others. Each first recess 4 is deep enough to allow a graft vessel having a diameter equal to or less than the width of that first recess 4 to enter that first recess 4 across substantially its entire diameter. Alternately, each first recess 4 is deep enough to allow a graft vessel having a diameter equal to or less than the width of that first recess 4 to enter that first recess 4 across at least half of its diameter. The depth of each first recess 4 is substantially the same. Alternately, the depth of at least one first recess 4 is different from the others. The length of each first recess 4 is not critical to the measurement tool 2. The surface of the measurement tool 2 adjacent to each first recess 4 may be engraved with a signifier 5 such as a number or letter associated with its dimensional width. Alternately, the signifiers 5 may be placed on the measurement tool 2 in another way. An arrow 7 may be placed adjacent each signifier 5, pointing to the first recess 4 associated with it.

At least one second recess 10 is also defined in the measurement tool 2. The second recess or recesses 10 are defined in the upper surface of the measurement tool 2, but instead could be defined in a side surface or in the bottom surface of the measurement tool 2. Alternately, where multiple second recesses 10 are provided, one or more second recesses 10 may be defined in a different surface of the measurement tool 2 than one or more other second recesses 10. The second recesses 10 are defined in the same surface of the measurement tool 2 as the first recesses 4. Alternately, the first recesses 4 and the second recesses 10 are defined in different surfaces of the measurement tool 2. The first recesses 4 and second recesses 10 are each grouped together, and separated from each other. Alternately, the first recesses 4 and second recesses 10 may be interleaved and clearly identified. Each second recess 10 has two sides 12 that are substantially parallel to one another. A bottom surface 14 of each second recess 10 is substantially perpendicular to both sides 12 of the second recess 10. However, the bottom surface 14 of at least one second recess 10 may be curved such that its sides 12 smoothly transition into a bottom surface 14 substantially without corners. The curved bottom surface 14 may have a semicircular cross-section or other curved cross-section. If multiple second recesses 10 are provided, each has a different width from the others. Each second recess 10 is deep enough to allow a graft vessel having a diameter equal to or less than the width of that second recess 10 to completely enter that second recess 10. Alternately, each second recess 10 is deep enough to allow a graft vessel having a diameter equal to or less than the width of that second recess 10 to enter that second recess 10 across at least half of its diameter. Where multiple second recesses 10 are provided, the depth of each second recess 10 is substantially the same. Alternately, the depth of at least one second recess 10 is different from the others. The length of each second recess 10 is not critical to the measurement tool 2. The surface of the measurement tool 2 adjacent to each second recess 10 may be engraved with a signifier 11 such as a number or letter associated with its dimensional width. Alternately, the one or more signifiers 11 may be placed on the measurement tool 2 in another way. An arrow 13 may be placed adjacent each signifier 11, pointing to the second recess 10 associated with it.

An indentation 16 is defined in one end of the measurement tool 2. The indentation 16 is substantially a section of a right cylinder having a radius of curvature. That is, the radius of curvature is substantially constant across the indentation 16. The indentation 16 is shaped to extend across at least half of the circumference of a tubular anatomic structure to be measured, where that tubular structure has a diameter less than or equal to a selected threshold, as is described in greater detail below. The axis 28 of the indentation 16 is offset from the longitudinal centerline 30 of the measurement tool 2. The indentation 16 has two ends 32, defining an opening between them. The ends 32 of the indentation 16 are substantially linear and parallel to one another, and therefore define a plane 34 between them, seen on edge in FIG. 2. This plane 34 defines the orientation of the opening of the indentation 16. The indentation 16 is oriented such that the plane 34 is at an angle other than perpendicular with regard to the longitudinal centerline 30 of the measurement tool 2. That is, the opening of the indentation 16 is said to be angled relative to the longitudinal centerline 30 of the measurement tool 2. By offsetting the indentation 16 relative to the longitudinal centerline 30 of the measurement tool 2, the body of the measurement tool 2 does not interfere with viewing the indentation 16 when it is used to measure a tubular structure. Alternately, the axis 28 of the indentation 16 is not offset from the centerline of the measurement tool 2, and/or the opening of the indentation 16 is not offset from the centerline 30 of the measurement tool 2. Alternately, the indentation 16 may be shaped differently. As one example, the indentation 16 may be U-shaped. As another example, the indentation 16 may have a diameter larger than the height and/or width of the body of the measurement tool 2, where ridges (not shown) extend outward from the indentation 16 in the body of the measurement tool 2 to assist in defining a section of a right cylinder or other shape. As another example, the ends 32 of the indentation 16 may be nonlinear or nonparallel. Alternately, the indentation 16 is formed to extend across less than half of the circumference of the tubular anatomic structure to be measured.

The indentation 16 may be provided at either end of the measurement tool 2. One or more additional indentations 16 may be defined in the measurement tool 2. If so, the indentations 16 may each have a different radius of curvature, in order to allow for the measurement of different types of tubular structures, or to more precisely measure the diameter of a tubular structure. Alternately, the indentations 16 all may have the same radius of curvature, in order to allow use of the measurement tool 2 in multiple orientations. For example, an identical indentation 16 may be provided at each end of the measurement tool 2. The surface of the measurement tool 2 adjacent to each indentation 16 may be engraved with a signifier 17 such as a number or letter associated with its dimensional width. Alternately, the at least one signifier 17 may be placed on the measurement tool 2 in another way.

The measurement tool 2 may be used to measure one or more tubular structures that are located within a patient, or that have been removed from a patient, or both. The usage of the measurement tool 2 is described below in the context of a CABG procedure. However, the use of the measurement tool 2 is not limited to such a procedure, and it may be used in a different procedure, such as a neurovascular procedure. The diameter and wall thickness of the graft vessel may be measured to determine whether it is over a threshold size. The graft vessel should have a certain minimum diameter to ensure that an adequate amount of blood can flow through it. Further, anastomotic devices advantageously may be used to connect the graft vessel to target vessels if the diameter and wall thickness of the graft vessel are within predetermined limits. The aorta may be measured to determine whether it is over a threshold size. A tool such as an aortic punch or cutter, whether used alone or integrated into an anastomosis device, delivery tool or system, can be used to create an opening in the wall of the aorta. Some tools enter the lumen of the aorta in the process of creating that opening. The travel of the tool into that lumen is a known, predetermined amount. By measuring the diameter of the aorta, a location can be selected for creating an opening in the aorta at which the diameter of the aorta is large enough to allow entry of the tool into its lumen without contacting its rear wall.

During a CABG procedure, one or more graft vessels are harvested from the patient. A graft vessel may be the saphenous vein, radial artery, left internal mammary artery, right internal mammary artery, or other vessel. An allograft or xenograft may be used as a graft vessel instead. After harvesting a graft vessel, it typically shrinks substantially as compared to its length and diameter before harvesting. The wall thickness of the graft vessel is measured first, when the graft vessel is in this deflated state. Where one second recess 10 is used, a user attempts to place the graft vessel into the second recess 10. If the graft vessel fits into the second recess 10, then its walls have a thickness equal to or less than half the width of that second recess 10. A single second recess 10 may be used, for example, where there is a single threshold value of the wall thickness that is important to the surgical procedure. For example, an anastomosis device may be utilized optimally with a graft vessel having a wall thickness less than or equal to a particular thickness. If so, the second recess 10 is substantially twice the width of that particular thickness. If the graft vessel cannot fit into that second recess 10, then its wall thickness is over the selected threshold. If the graft vessel fits into that second recess 10 snugly, then its wall thickness is at the selected threshold. Otherwise, the wall thickness of the graft vessel is under the selected threshold. Where multiple second recesses 10 are used to measure wall thickness, the graft vessel is placed in successive second recesses 10 until it fits within a second recess 10 without perceptible space between it and the walls of the second recess 10. The wall thickness of that graft vessel is thus substantially half of the width of that second recess 10.

Next, to measure the diameter of the harvested graft vessel, the graft vessel is perfused with saline, blood or other biocompatible liquid. Clamps, clips or other devices may be used to keep the liquid inside the graft vessel. When vasospasm is present, pressure inside the graft vessel is increased to the point at which vasospasm is overcome. The graft vessel inflates substantially to its normal size, so that its diameter can be measured. A user then attempts to place the graft vessel into one of the first recesses 4. If the graft vessel has a diameter that is too large to allow it to fit into that first recess 4, then the graft vessel is moved to a larger first recess 4, and the attempt is made again. If the graft vessel has a diameter smaller than the first recess 4, such that there is perceptible space between the graft vessel and the walls 6 of the first recess, then the graft vessel is moved to a smaller first recess 4, and the attempt is made again. If the graft vessel fits within the first recess 4 without perceptible space between it and the walls of the first recess 4, then the diameter of that graft vessel is substantially equal to the width of that first recess 4. If a single first recess 4 is used, having a width corresponding to a selected threshold, and the graft vessel cannot fit into that first recess 4, then its diameter is over the selected threshold. If the graft vessel fits into that first recess 4 snugly, then its diameter is at the selected threshold. Otherwise, the diameter of the graft vessel is under the selected threshold. The diameter of the graft vessel may be important in determining the suitability of a graft vessel for use with one or more anastomosis devices or tools for deploying anastomosis devices. For example, an anastomosis tool having a cavity through which the graft vessel is pulled may be able to accommodate graft vessels at or under a particular diameter. In another embodiment, the diameter of the graft vessel is measured before the wall thickness of the graft vessel. The measurement tool 2 is capable of measuring multiple characteristics of the graft vessel in any order.

Figure 5:
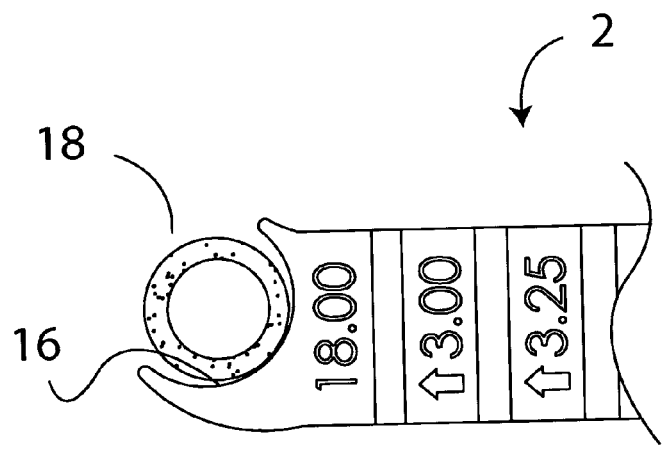
FIG. 5 is a side view of the measurement tool showing the indentation relative to a tubular structure to be measured.

Referring also to FIG. 5, the indentation 16 then is used to measure the diameter of the aorta 18. However, this measurement may be performed before or after the overall thickness of the graft vessel and/or the wall thickness of the graft vessel is measured. This position on the aorta 18 may be referred to as the proximal anastomosis site. The indentation 16 is placed against the aorta 18, facing outward toward the user. In this way, the user can better visualize the fit between the aorta 18 and the indentation 16. If the aorta is positioned loosely in the indentation 16 with space between the aorta 18 and the indentation 16, as is shown in FIG. 5, then the aorta 18 has a radius that is smaller than the radius of curvature of the indentation 16. If the indentation 16 fits snugly onto or does not fit onto the aorta 18, then the aorta 18 has a radius that is at least as large as the radius of curvature of the indentation 16. Thus, the aorta 18 or other tubular structure can be checked in one step to determine whether its radius, and hence its diameter, is larger than, smaller than or equal to a selected value.

While a measurement tool 2 has been described having recesses 4, 10 and an indentation 16, the measurement tool 2 need not include all of these measurement features, and instead may include one or more of them in a number of combinations. For example, in one embodiment, the measurement tool 2 includes one or more first recesses 4 and the indentation 16, but does not includes second recesses 10. In another embodiment, the measurement tool 2 includes only the indentation 16 as described above, but does not include recesses 4, 10. In another embodiment, the measurement tool 2 includes only the second recesses 10 as described above, but does not include the indentation 16 or the first recesses 4. In another embodiment, the measurement tool 2 includes the second recesses 10 and the indentation 16, but does not include the first recesses 4. In another embodiment, the measurement tool 2 includes the first recesses 4 and the second recesses 10, but does not include the indentation 16.

Figure 6:
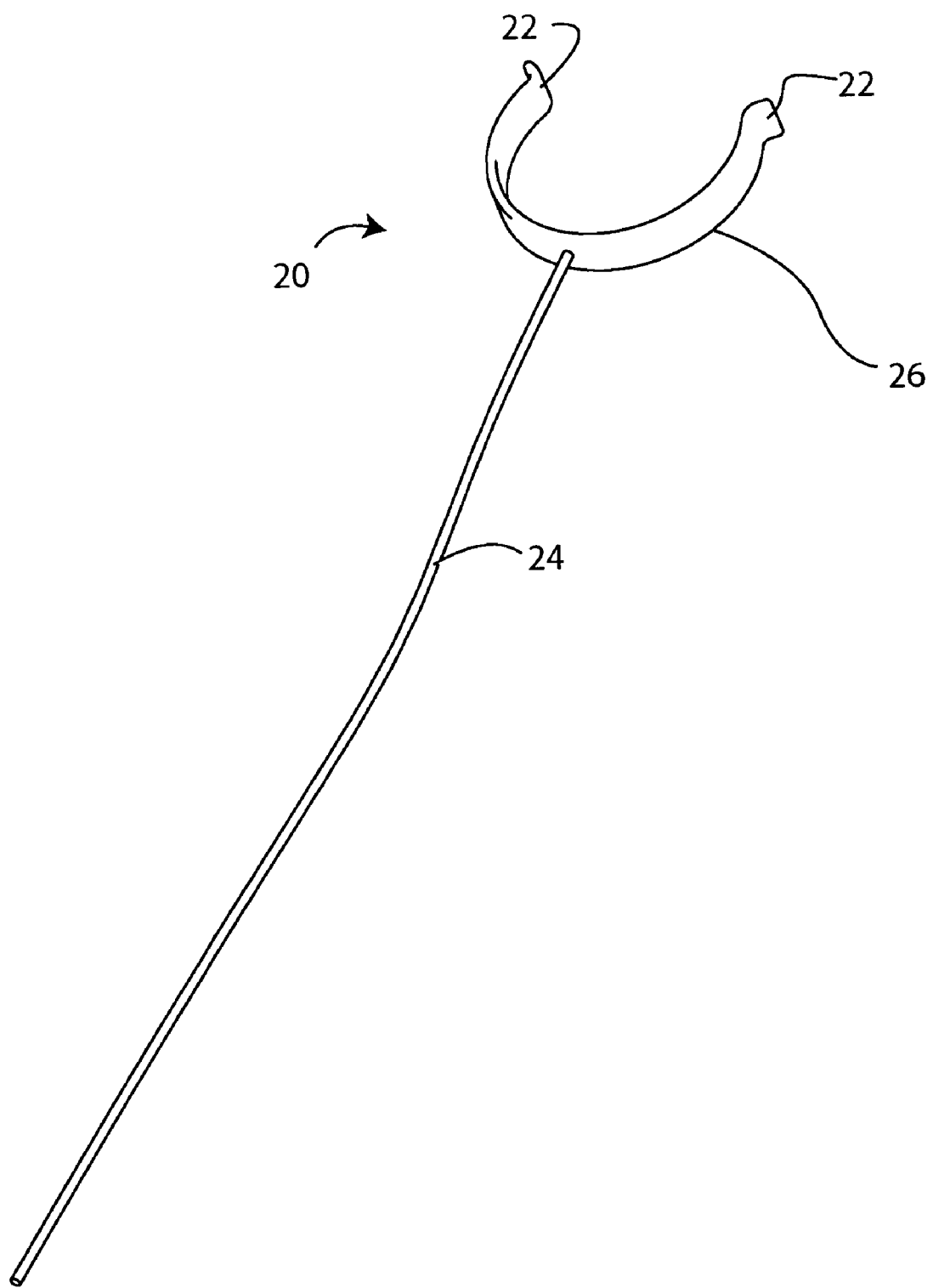
FIG. 6 is a perspective view of another embodiment of a measurement tool.

Referring to FIG. 6, in another embodiment, another embodiment of a measurement tool 20 is used during minimally invasive surgery. The measurement tool 20 is sized such that it can pass through an opening or a trocar port (not shown) providing access to the thoracic cavity of a patient. The measurement tool 20 may be constructed to be thin and/or flexible to facilitate its insertion into and removal from the thoracic cavity through the opening or trocar port. The measurement tool 20 includes a clip 26 that is sized to fit onto the aorta or other anatomic structure to be measured, and to extend around at least half of the circumference of that anatomic structure. Flanges 22 may flare outward smoothly from the ends of the clip 26. The use of these flanges 22, and the smooth curvature between the clip 26 and these flanges 22, minimizes or eliminates any damage to the tubular anatomic structure being measured. The clip 26 has a diameter equal to a selected threshold value. The surgeon attempts to place the clip 26 onto a candidate proximal anastomosis site on the aorta, using an endoscopic forceps or other tool. The proximal anastomosis site is the location on the aorta to which a graft vessel is to be attached. If the clip 26 cannot firmly clip onto the aorta, then the diameter of the aorta is less than the diameter of the clip 26, and hence less than the selected threshold value. Thus, the aorta does not have an appropriate diameter at that location, and another proximal anastomosis site is chosen and measured. If the clip 26 can firmly clip onto the aorta, then the diameter of the aorta is equal to or greater than the diameter of the clip 26, and hence at least equal to the selected threshold value. Thus, the aorta has an appropriate diameter at that location, and that proximal anastomosis site may be utilized.

The measurement tool 20 also includes a tail 24. The tail 24 is a flexible length of biocompatible material, fixed at one end to the clip 26. The tail 24 may include one or more distance markers or signifiers thereon. If the aorta has an acceptable diameter at a proximal anastomosis site, then the clip 26 is left in place on the aorta. The surgeon utilizes an endoscopic forceps or other tool to grip the tail 24 and drag the gripped point toward a distal anastomosis site. The distal anastomosis site is the location on a coronary artery to which a graft vessel is to be attached. Because the heart has a complex shape that varies between patients, the flexibility of the tail 24 allows the distance between the proximal anastomosis site and the distal anastomosis site to be measured. If the point at which the tail 24 is gripped defines a length with respect to the fixed end of the tail 24 that is inadequate to reach the distal anastomosis site, the surgeon releases the tail 24 and grips it again further away from its fixed end. If the point at which the tail 24 is gripped defines a length that is at least as far as the distance between the proximal anastomosis site and the distal anastomosis site, then the surgeon may place the tail 24 against the heart and read the appropriate distance marker on the tail 24 that is closest to the distal anastomosis site. Alternately, the surgeon may release the tail 24 and grip it again closer to the fixed end of the tail 24. Thus, the distance between the proximal anastomosis site and the distal anastomosis site can be determined. This distance is substantially equivalent to the minimum length for the graft vessel. The clip 26 is then removed from the aorta and extracted from the thoracic cavity. If multiple graft vessels are to be placed, the measurement tool 20 instead may be moved to another potential proximal anastomosis site, and the length of another graft vessel to another distal anastomosis site is determined in the same way as described above.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A method of measuring a tissue structure having walls and a lumen therethrough, comprising:

providing a body having at least one recess defined therein, wherein each said recess has a width corresponding to a different wall thickness of the tissue structure;

bringing inner surfaces of the walls of the tissue structure together, the tissue structure being in a flaccid state;

moving at least a portion of the tissue structure relative to at least one said recess to measure the wall thickness thereof;

inflating the tissue structure; and then measuring its diameter.

2. The method of claim 1, wherein said moving comprises directing the flaccid tissue structure successively toward a plurality of said recesses until said tissue structure is unable to fit into any of said recesses.

3. The method of claim 1, wherein said moving comprises directing the flaccid tissue structure successively toward a plurality of said recesses until said tissue structure is unable to fit substantially snugly into any of said recesses.

4. The method of claim 1, wherein said inflating is performed by introducing biocompatible fluid into the tissue structure.

5. The method of claim 4, wherein said biocompatible fluid is saline solution.

6. The method of claim 1, wherein said measuring comprises moving the inflated tissue structure relative to at least one said recess to measure at least one characteristic thereof.

7. The method of claim 6, wherein said moving comprises directing the inflated tissue structure successively toward a plurality of said recesses until said tissue structure is unable to fit into any of said recesses.

8. The method of claim 6, wherein said moving comprises directing the inflated tissue structure successively toward a plurality of said recesses until said tissue structure is unable to fit substantially snugly into any of said recesses.

9. The method of claim 6, wherein said moving comprises directing the inflated tissue structure successively toward at least one said recess until said tissue structure fits substantially snugly into one of said recesses.

10. The method of claim 9, wherein said body includes at least one measurement indicia adjacent to each said recess, further comprising reading said measurement indicia adjacent to said recess into which said inflated tissue structure fits substantially snugly.

* * * * *